(12) United States Patent
Bhat

(10) Patent No.: US 11,576,002 B2
(45) Date of Patent: Feb. 7, 2023

(54) SENSOR HUB IN CONNECTOR PLUG OR CABLE FOR A HEARING ASSISTANCE DEVICE

(71) Applicant: Starkey Laboratories, Inc., Eden Prairie, MN (US)

(72) Inventor: Sudeep Sunder Bhat, Chanhassen, MN (US)

(73) Assignee: Starkey Laboratories, Inc., Eden Prairie, MN (US)

( * ) Notice: Subject to any disclaimer, the term of this patent is extended or adjusted under 35 U.S.C. 154(b) by 231 days.

(21) Appl. No.: 17/247,571

(22) Filed: Dec. 16, 2020

(65) Prior Publication Data

US 2021/0185460 A1  Jun. 17, 2021

Related U.S. Application Data

(60) Provisional application No. 62/949,129, filed on Dec. 17, 2019.

(51) Int. Cl.
| | | |
|---|---|---|
| *H04R 25/00* | (2006.01) | |
| *A61B 5/0205* | (2006.01) | |
| *A61B 5/00* | (2006.01) | |
| *A61B 5/332* | (2021.01) | |
| *A61B 5/145* | (2006.01) | |

(Continued)

(52) U.S. Cl.
CPC ......... *H04R 25/60* (2013.01); *A61B 5/02055* (2013.01); *A61B 5/6817* (2013.01); *A61B 5/02125* (2013.01); *A61B 5/02438* (2013.01); *A61B 5/0533* (2013.01); *A61B 5/14542* (2013.01); *A61B 5/332* (2021.01);

(Continued)

(58) Field of Classification Search
CPC .. H04R 1/1033; H04R 25/556; H04R 25/603; H04R 25/609; H04R 2225/021; H04R 2225/0213; H04R 2225/026; H04R 2225/57; H04R 2225/61; H04R 2225/77; H01R 13/66
See application file for complete search history.

(56) References Cited

U.S. PATENT DOCUMENTS 6,181,801 B1 * 1/2001 Puthuff ................ H04R 25/505
381/384
9,990,172 B2 * 6/2018 Komaromi ........... H04R 25/305
(Continued)

FOREIGN PATENT DOCUMENTS

| CN | 106963548 A | * | 7/2017 | ........... A61B 5/0022 |
| WO | WO-2021086538 A1 | * | 5/2021 | ........... H04R 1/1008 |

*Primary Examiner* — Ryan Robinson
(74) *Attorney, Agent, or Firm* — Schwegman Lundberg & Woessner, P.A.

(57) ABSTRACT

Disclosed herein, among other things, are apparatus and methods for a hearing assistance device with a sensor hub. Various aspects of the present subject matter include a method of using a hearing assistance device. A method includes sensing biometric signals from a wearer of a hearing assistance device using one or more sensor modules included in or on a receiver housing of the hearing assistance device, the receiver housing configured to connect to an end of a cable and configured to be placed in or near an ear canal of the wearer. The method also includes transmitting data indicative of the sensed biometric signals from the one or more sensor modules to a sensor hub in a connector of the cable, and processing the data using the sensor hub.

20 Claims, 5 Drawing Sheets

(51) Int. Cl.
*A61B 5/021* (2006.01)
*A61B 5/024* (2006.01)
*A61B 5/0533* (2021.01)

(52) U.S. Cl.
CPC .......................... *A61B 2562/0219* (2013.01); *H04R 2225/023* (2013.01); *H04R 2225/57* (2019.05)

(56) References Cited

U.S. PATENT DOCUMENTS

| | | | |
|---|---|---|---|
| 10,028,066 B2* | 7/2018 | Schmidt | H04R 25/70 |
| 10,409,545 B1* | 9/2019 | Olson | G06F 3/162 |
| 11,089,412 B2* | 8/2021 | De Haan | A61B 5/6817 |
| 11,115,764 B2* | 9/2021 | Silberzahn | A61B 5/6815 |
| 11,265,643 B2* | 3/2022 | Higgins | H04R 25/70 |
| 11,350,211 B2* | 5/2022 | Pedersen | H04R 25/55 |
| 2007/0014423 A1* | 1/2007 | Darbut | H04R 25/65 |
| | | | 381/330 |
| 2017/0180882 A1* | 6/2017 | Lu | H04R 25/558 |
| 2018/0368722 A1* | 12/2018 | Lu | A61B 5/398 |
| 2020/0314520 A1* | 10/2020 | Rhondeau | H04R 1/1016 |
| 2020/0374641 A1* | 11/2020 | Husung | H04R 25/609 |
| 2021/0092530 A1* | 3/2021 | Thomsen | H04R 25/50 |
| 2021/0100508 A1* | 4/2021 | Vos | H04R 25/603 |
| 2021/0168539 A1* | 6/2021 | Stephenson | A61B 5/0205 |
| 2022/0014834 A1* | 1/2022 | Au | H04R 1/1041 |
| 2022/0141603 A1* | 5/2022 | Schmidt | H04R 25/43 |
| | | | 381/323 |
| 2022/0248147 A1* | 8/2022 | Talaslian | H04R 25/656 |
| 2022/0287639 A1* | 9/2022 | Mostafaei | H04R 25/60 |

* cited by examiner

SENSOR HUB IN CONNECTOR PLUG OR CABLE FOR A HEARING ASSISTANCE DEVICE

CROSS-REFERENCE TO RELATED APPLICATION

This patent application claims the benefit of U.S. Provisional Patent Application No. 62/949,129, filed Dec. 17, 2019, which is incorporated by reference herein in its entirety.

TECHNICAL FIELD

This document relates generally to hearing assistance systems and more particularly to a sensor hub for hearing assistance device applications.

BACKGROUND

Examples of hearing assistance devices, also referred to herein as hearing devices or hearing instruments, include both prescriptive devices and non-prescriptive devices. Specific examples of hearing assistance devices include, but are not limited to, hearing aids, headphones, assisted listening devices, and earbuds.

Hearing aids are used to assist patients suffering hearing loss by transmitting amplified sounds to ear canals. In one example, a hearing aid is worn in and/or around a patient's ear. Hearing aids may include processors and electronics that improve the listening experience for a specific wearer or in a specific acoustic environment.

In addition, biometric sensors may be included in or on a hearing instrument to collect physiological data from the wearer. Additional processing is needed to analyze collected physiological data. Generally, hearing aids are small and require extensive design to fit all the necessary electronic components into the hearing aid or attached to the hearing aid.

There is a need in the art for an improved processing system for hearing assistance device applications.

SUMMARY

Disclosed herein, among other things, are apparatus and methods for a hearing assistance device with a sensor hub. In various embodiments, a hearing assistance device may include a first housing configured to be worn above an ear of a wearer, the first housing including hearing assistance electronics, and a second housing configured to be worn in the ear of the wearer, the second housing including a receiver configured to output signals processed by the hearing assistance electronics. The device may also include a cable configured to connect to the first housing at a first end and to the second housing at the second end. The device may further include one or more sensor modules at or near the second end of the cable, the one or more sensor modules configured to sense biometric signals from the wearer. The device may also include a sensor hub at or near the first end of the cable, the sensor hub including a processor configured to process data from the one or more sensor modules.

Various aspects of the present subject matter include a method of using a hearing assistance device. The method may include sensing biometric signals from a wearer of a hearing assistance device using one or more sensor modules included in or on a receiver housing of the hearing assistance device, the receiver housing configured to connect to an end of a cable and configured to be placed in or near an ear canal of the wearer. The method may also include transmitting data indicative of the sensed biometric signals from the one or more sensor modules to a sensor hub in a connector of the cable, and processing the data using the sensor hub.

This Summary is an overview of some of the teachings of the present application and not intended to be an exclusive or exhaustive treatment of the present subject matter. Further details about the present subject matter are found in the detailed description and appended claims. The scope of the present invention is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Figure 1:
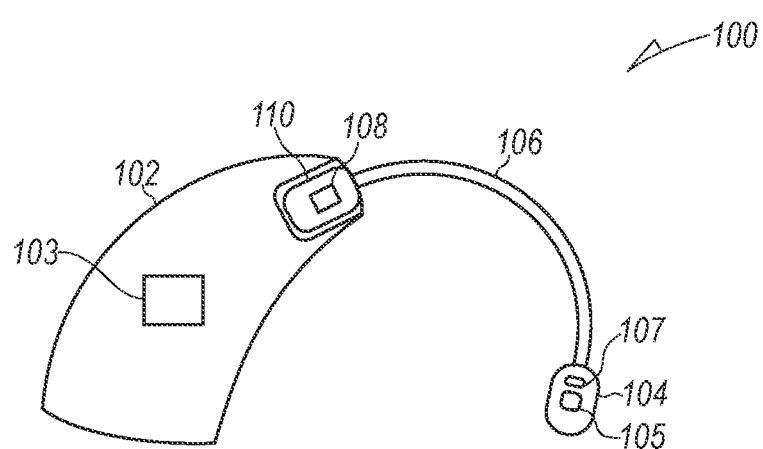
FIG. 1 illustrates a hearing assistance device with a sensor hub, according to various embodiments of the present subject matter.

The following detailed description of the present subject matter refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is demonstrative and not to be taken in a limiting sense. The scope of the present subject matter is defined by the appended claims, along with the full scope of legal equivalents to which such claims are entitled.

The present detailed description will discuss hearing assistance devices using the example of hearing aids. Other hearing assistance devices include, but are not limited to, those in this document. It is understood that their use in the description is intended to demonstrate the present subject matter, but not in a limited or exclusive or exhaustive sense.

One example of a hearing assistance device is a receiver-in-the-canal (RIC) hearing aid. In various embodiments, a sensor hub provides a computational node to process raw sensor data from RIC sensor modules. Currently, there are two approaches to process the raw sensor data, either using the hearing aid's main processor, or using a processor of a smartphone wirelessly connected to the hearing aid. However, processing of raw sensor data is performed by complex algorithms that are memory and process intensive with tight timing requirements, which can overload an existing processor or cause other processing to be delayed or discontinued. Having a dedicated sensor hub as described herein provides for processing of raw sensor data without occupying a large memory footprint at the main hearing aid processor or having to transport large amount of raw sensor data over a wireless link between the hearing aid and the smartphone. Placing such a sensor hub in the receiver housing configured to be placed in the wearer's ear has the disadvantage of causing fitment issues due to increased size of the sensor hub assembly, and adding more electronics such as an external crystal for better clock accuracy would further increase the space needed in the receiver housing. Placing a sensor hub with the hearing assistance electronics, such as on a hearing aid flex circuit, has several drawbacks, notably that not all hearing aid devices use the sensor hub which adds wasted cost to the design, and adding the sensor hub can increase flex circuit size with additional pinouts. If the sensor hub is not populated on all hearing aids, then manufacturing and inventory management would have to maintain different variants of the same design.

Thus, the present subject matter provides for placing the sensor hub in a RIC cable or in the connector at the end of the cable. The cable may be configured to connect, to an above-the-ear housing at one end and to an in-the-ear housing at the opposite end, using one or more connectors at the respective cable ends. The sensor hub may include at least one processor and memory configured to store data and instructions executed by the at least one processor, in various embodiments. By placing the sensor hub in the cable or in the connector at an end of the cable, adding or replacing the sensor hub for more processing power or other desired attributes does not have to incur cost of redesigning the layout of components in a hearing aid, thereby saving development costs. Further, if the sensor hub is placed in the receiver housing, there is a potential to produce heat that can interfere with sensitive thermistors for temperature sensing. Placing the sensor hub in the cable or in the connector at an end of the cable, as described herein, avoids the problem of excessive heat.

In various embodiments, the present subject matter provides a sensor hub in the RIC-side of the connector cable and may use a serial interface over the cable to communicate with sensor modules in a receiver housing configured to be inserted in an ear canal of a wearer. The sensor hub may be placed near either end of the cable, or in a connector at either end of the cable, in various embodiments. The sensor module may be configured to convert an analog signal and transform it into digital data, in various embodiments. According to various embodiments, the data may be transported from the sensor module over a serial bus such as I2C for processing in the sensor hub. The sensor hub may process or collate data from multiple sensors and store the data into logs for later retrieval, in various embodiments. In some embodiments, the hearing aid's main processor may request logs periodically to be sent to a smartphone when tethered, or the smartphone may request the hearing aid to obtain the data on demand.

FIG. 1 illustrates a hearing assistance device with a sensor hub, according to various embodiments of the present subject matter. In various embodiments, a hearing assistance device 100 may include a first housing 102 configured to be worn above an ear of a wearer, the first housing 102 including hearing assistance electronics 103, and a second housing 104 configured to be worn in the ear of the wearer, the second housing 104 including a receiver 107 configured to output signals processed by the hearing assistance electronics 103. The device 100 may also include a cable 106 configured to connect to the first housing 102 at a first end and to the second housing 104 at the second end. The device 100 may further include one or more sensor modules 105 at or near the second end of the cable, the one or more sensor modules 105 configured to sense biometric signals from the wearer. The device may also include a sensor hub 108 at or near the first end of the cable, the sensor hub 108 including a processor configured to process data from the one or more sensor modules.

According to various embodiments, the sensor hub 108 may be included in the cable 106. In the depicted embodiment, the sensor hub 108 is included in a connector plug 110 at the first end of the cable 106. The sensor hub 108 may be configured to communicate with the one or more sensor modules 105 using a serial interface over the cable 106, in various embodiments. According to various embodiments, the sensor hub 108 may be configured to process or collate data from the one or more sensor modules 105 and store the processed or collated data in one or more logs. The one or more logs may be configured for transmission to the hearing assistance electronics 103, in various embodiments. In some embodiments, the one or more logs may be configured for continuous transmission to the hearing assistance electronics 103. The one or more logs may be configured for on-demand transmission to the hearing assistance electronics 103, in some embodiments. In various embodiments, the device may include an inter-integrated circuit (I2C) bus connection from the hearing assistance electronics 103 to the sensor hub 108. The cable 106 may include an I2C bus connection from the sensor hub 108 to the one or more sensor modules 105, in various embodiments. According to various embodiments, the hearing assistance device 100 may be a receiver-in-the-canal (RIC) hearing aid.

Figure 2:
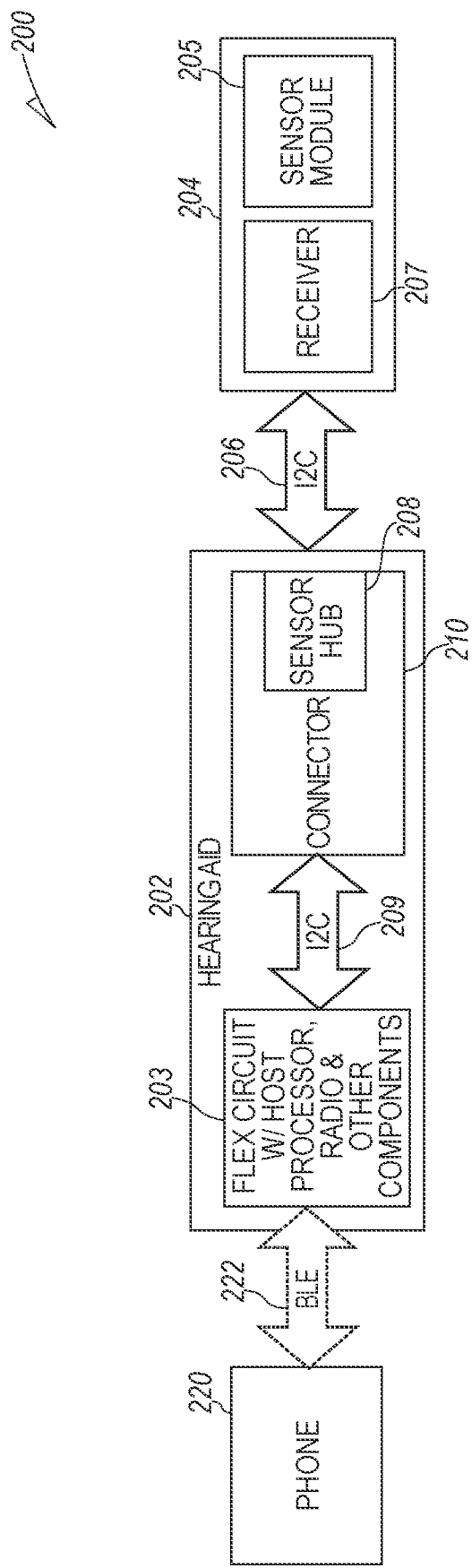
FIG. 2 illustrates a block diagram of a hearing assistance system including a sensor hub, according to various embodiments of the present subject matter.

FIG. 2 illustrates a block diagram of a hearing assistance system including a sensor hub, according to various embodiments of the present subject matter. In various embodiments, a hearing assistance system 200 may include a first housing 202 configured to be worn above an ear of a wearer, the first housing 202 including hearing assistance electronics 203, and a second housing 204 configured to be worn in the ear of the wearer, the second housing 204 including a receiver 207 configured to output signals processed by the hearing assistance electronics 203. The system 200 may also include a cable 206 configured to connect to the first housing 202 at a first end and to the second housing 204 at the second end. The system 200 may further include one or more sensor modules 205 in the second housing, the one or more sensor modules 205 configured to sense biometric signals from the wearer. The system 200 may also include a sensor hub 208 in a connector 210 of the cable 206, the connector 210 configured to be inserted into the first housing 202. The sensor hub 208 may include a processor configured to process data from the one or more sensor modules 205, and a memory configured to store data and instructions to be executed by the processor, in various embodiments.

According to various embodiments, the cable 206 includes an I2C bus connection. The hearing assistance electronics 203 may be connected to the sensor hub using an I2C bus connection 209, in various embodiments. In some embodiments, the hearing assistance electronics 203 include a radio circuit and antenna for wireless communication 222 with an external device 220. In various embodiments, the wireless communication 222 includes a Bluetooth Low Energy (BLE) protocol. Other types of wireless communication protocols may be used without departing from the scope of the present subject matter. In some embodiments, the external device 220 includes a smartphone. Other types of external devices, including but not limited to tablets, video streamers, and/or beacons, may be used without departing from the scope of the present subject matter.

In various embodiments, the RIC sensor module located in the ear or ear canal may sample biological signals from the hearing aid wearer. The collected sample may be converted from an analog representation of the signal to digital bytes that are transferred to sensor hub, in various embodiments. The sensor hub provides a computational node for algorithms that process raw sensor data from RIC sensor modules in the ear, in various embodiments. According to various embodiments, the processed data may be stored in logs that may be retrieved on demand (by the hearing assistance electronics or by a processor of an external device) or streamed in real-time, depending on the feature and use case. The present subject matter provides a modular sensor hub design that may be configured to work with multiple vendor's stock RIC devices and for internal solutions with custom hearing assistance shells, in various embodiments. The present subject matter may be used to extend the biological sensing features for various RIC cables without altering the existing firmware architecture to support future sensor needs, in some embodiments.

Figure 3:
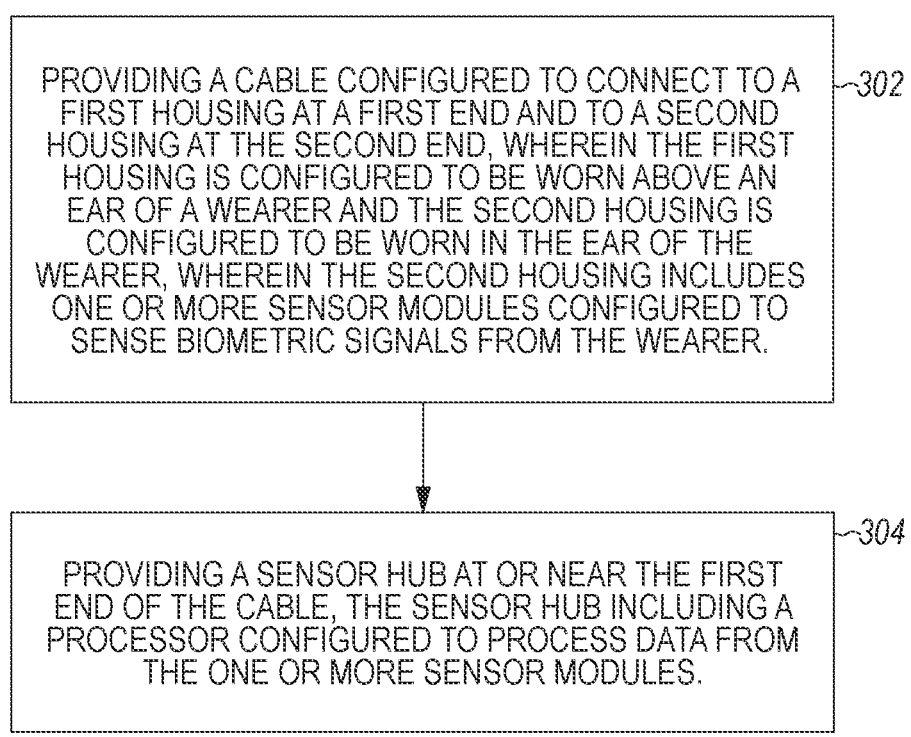
FIG. 3 illustrates a flow diagram of a method of forming a portion of a hearing assistance device, according to various embodiments of the present subject matter.

FIG. 3 illustrates a flow diagram of a method of forming a portion of a hearing assistance device, according to various embodiments of the present subject matter. The method 300 may include, at step 302, providing a cable configured to connect to a first housing at a first end and to a second housing at the second end, wherein the first housing is configured to be worn above an ear of a wearer and the second housing configured to be worn in the ear of the wearer, wherein the first housing includes hearing assistance electronics and the second housing includes a receiver configured to output signals processed by the hearing assistance electronics and one or more sensor modules configured to sense biometric signals from the wearer. The method 300 may also include, at step 304, providing a sensor hub at or near the first end of the cable, the sensor hub including a processor configured to process data from the one or more sensor modules.

According to various embodiments, at least one of the one or more sensor modules includes a heart rate sensor, a temperature sensor, an inertial measurement unit (IMU), a blood pressure sensor, a galvanic skin response (GSR) sensor, a pulse transit time (PTT) sensor, an oxygen (O2) sensor, an electrocardiogram (ECG), or a blood glucose sensor. Other types of sensors, or any combination of the enumerated sensors and/or other types of sensors, may be used without departing from the scope of the present subject matter.

Figure 4:
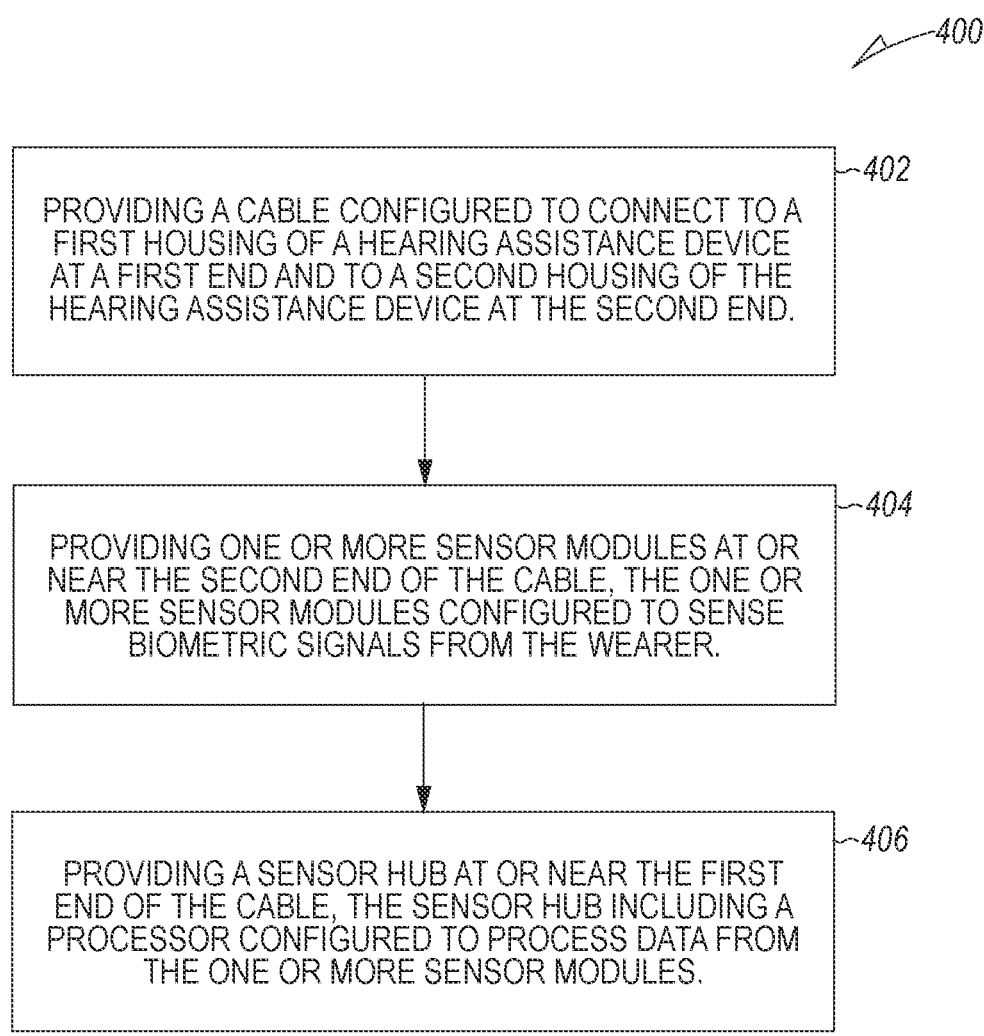
FIG. 4 illustrates a flow diagram of a method of forming a hearing assistance system, according to various embodiments of the present subject matter.

FIG. 4 illustrates a flow diagram of a method of forming a hearing assistance system, according to various embodiments of the present subject matter. The method 400 may include, at step 402, providing a cable configured to connect to a first housing of a hearing assistance device at a first end and to a second housing of a hearing assistance device at the second end. The method may also include, at step 404, providing one or more sensor modules at or near the second end of the cable, the one or more sensor modules configured to sense biometric signals from the wearer. The method may further include, at step 406, providing a sensor hub at or near the first end of the cable, the sensor hub including a processor configured to process data from the one or more sensor modules.

Figure 5:
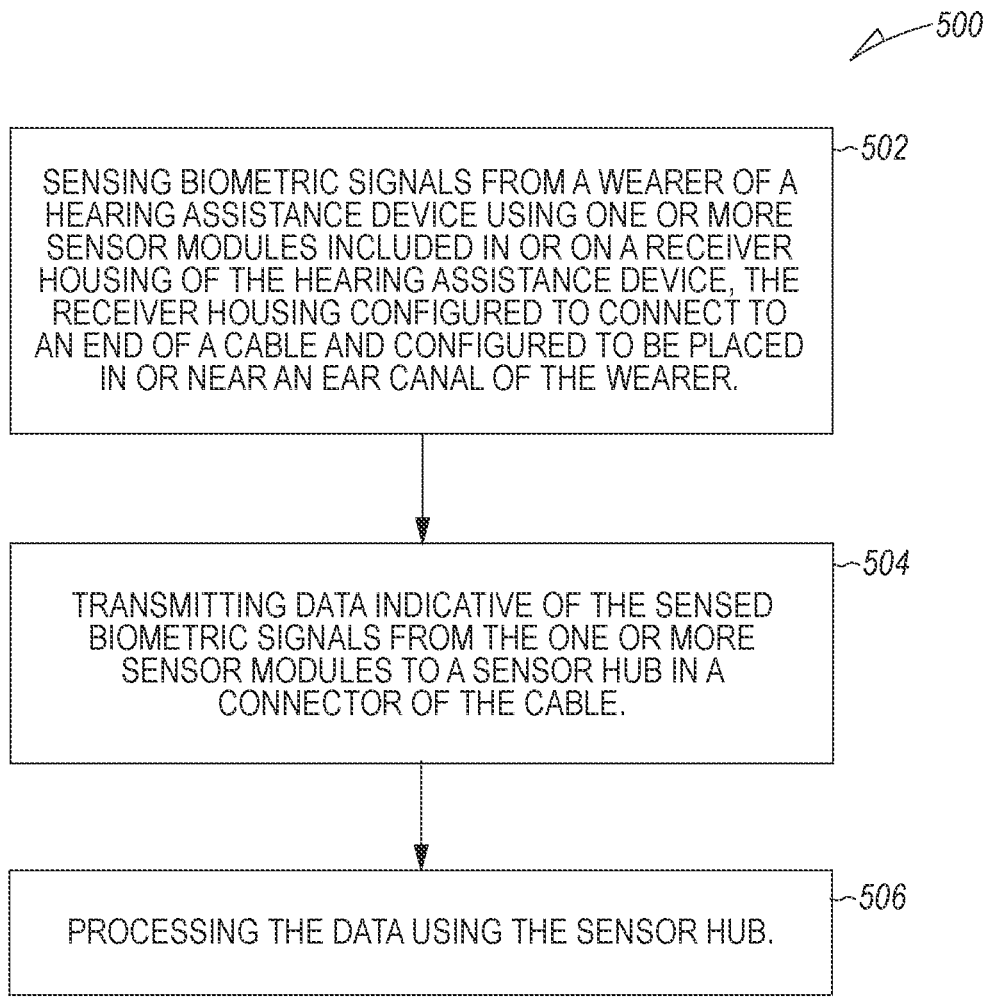
FIG. 5 illustrates a flow diagram of a method of using a hearing assistance device, according to various embodiments of the present subject matter.

FIG. 5 illustrates a flow diagram of a method of using a hearing assistance device, according to various embodiments of the present subject matter. The method 500 may include, at step 502, sensing biometric signals from a wearer of a hearing assistance device using one or more sensor modules included in or on a receiver housing of the hearing assistance device, the receiver housing configured to connect to an end of a cable and configured to be placed in or near an ear canal of the wearer. The method may also include, at step 504, transmitting data indicative of the sensed biometric signals from the one or more sensor modules to a sensor hub in a connector of the cable, and processing the data using the sensor hub, at step 506.

According to various embodiments, the sensor hub may be incorporated into a receiver-in-the-canal (RIC) hearing aid, a behind-the-ear (BTE) hearing aid, a personal sound amplification product (PSAP), an over-the-counter (OTC) hearing device, headphones, hearables, or the like. Other types of hearing assistance devices may include the sensor hub without departing from the scope of the present subject matter.

Benefits of the present subject matter include reducing the amount of memory needed for the hearing assistance device processor, and preventing waste of resources that would otherwise support development of more complex hearing assistance device applications. Moreover, not all hearing assistance devices need to support this sensor feature set, which makes the footprint even more wasteful. By transporting processed feature data instead of raw data to an external device, less BLE bandwidth may be used. In addition, having a dedicated sensor hub may allow a sensor system to be maintained independent of other hearing aid applications, thereby saving time and cost for development and maintenance. An additional benefit of the dedicated sensor hub of the present subject matter includes insured system stability by limiting the use of SOUP (software of unknown provenance), and ensuring compliance with regulatory requirements and program schedules. Further, the present subject matter enables the reuse of a common sensor hub solution for hosting externally sourced vendor algorithms for stock RIC cables.

Various embodiments of the present subject matter support wireless communications with a hearing assistance device. In various embodiments the wireless communications may include standard or nonstandard communications. Some examples of standard wireless communications include link protocols including, but not limited to, Bluetooth™, Bluetooth™ Low Energy (BLE), IEEE 802.11 (wireless LANs), 802.15 (WPANs), 802.16 (WiMAX), cellular protocols including, but not limited to CDMA and GSM, ZigBee, and ultra-wideband (UWB) technologies. Such protocols support radio frequency communications and some support infrared communications. Although the present system is demonstrated as a radio system, it is possible that other forms of wireless communications may be used such as ultrasonic, optical, infrared, and others. It is understood that the standards which may be used include past and present standards. It is also contemplated that future versions of these standards and new future standards may be employed without departing from the scope of the present subject matter.

The wireless communications support a connection from other devices. Such connections include, but are not limited to, one or more mono or stereo connections or digital connections having link protocols including, but not limited to 802.3 (Ethernet), 802.4, 802.5, USB, SPI, PCM, ATM, Fibre-channel, Firewire or 1394, InfiniBand, or a native streaming interface. In various embodiments, such connections include all past and present link protocols. It is also contemplated that future versions of these protocols and new future standards may be employed without departing from the scope of the present subject matter.

Hearing assistance devices typically include at least one enclosure or housing, a microphone, hearing assistance device electronics including processing electronics, and a speaker or "receiver." Hearing assistance devices may include a power source, such as a battery. In various embodiments, the battery is rechargeable. In various embodiments multiple energy sources are employed. It is understood that in various embodiments the microphone is optional. It is understood that in various embodiments the receiver is optional. It is understood that variations in communications protocols, antenna configurations, and combinations of components may be employed without departing from the scope of the present subject matter. Antenna configurations may vary and may be included within an enclosure for the electronics or be external to an enclosure for the electronics. Thus, the examples set forth herein are intended to be demonstrative and not a limiting or exhaustive depiction of variations.

It is understood that digital hearing assistance devices include a processor. In digital hearing assistance devices with a processor, programmable gains may be employed to adjust the hearing assistance device output to a wearer's particular hearing impairment. The processor may be a digital signal processor (DSP), microprocessor, microcontroller, other digital logic, or combinations thereof. The processing may be done by a single processor, or may be distributed over different devices. The processing of signals referenced in this application may be performed using the processor or over different devices. Processing may be done in the digital domain, the analog domain, or combinations thereof. Processing may be done using subband processing techniques. Processing may be done using frequency domain or time domain approaches. Some processing may involve both frequency and time domain aspects. For brevity, in some examples drawings may omit certain blocks that perform frequency synthesis, frequency analysis, analog-to-digital conversion, digital-to-analog conversion, amplification, buffering, and certain types of filtering and processing. In various embodiments of the present subject matter the processor is adapted to perform instructions stored in one or more memories, which may or may not be explicitly shown. Various types of memory may be used, including volatile and nonvolatile forms of memory. In various embodiments, the processor or other processing devices execute instructions to perform a number of signal processing tasks. Such embodiments may include analog components in communication with the processor to perform signal processing tasks, such as sound reception by a microphone, or playing of sound using a receiver (i.e., in applications where such transducers are used). In various embodiments of the present subject matter, different realizations of the block diagrams, circuits, and processes set forth herein may be created by one of skill in the art without departing from the scope of the present subject matter.

It is further understood that different hearing assistance devices may embody the present subject matter without departing from the scope of the present disclosure. The devices depicted in the figures are intended to demonstrate the subject matter, but not necessarily in a limited, exhaustive, or exclusive sense. It is also understood that the present subject matter may be used with a device designed for use in the right ear or the left ear or both ears of the wearer.

The present subject matter is demonstrated for hearing assistance devices, including hearing assistance devices, including but not limited to, behind-the-ear (BTE), in-the-ear (ITE), in-the-canal (ITC), receiver-in-canal (RIC), invisible-in-canal (IIC) or completely-in-the-canal (CIC) type hearing assistance devices. It is understood that behind-the-ear type hearing assistance devices may include devices that reside substantially behind the ear or over the ear. Such devices may include hearing assistance devices with receivers associated with the electronics portion of the behind-the-ear device, or hearing assistance devices of the type having receivers in the ear canal of the user, including but not limited to receiver-in-canal (RIC) or receiver-in-the-ear (RITE) designs. The present subject matter may also be used in hearing assistance devices generally, such as cochlear implant type hearing devices. The present subject matter may also be used in deep insertion devices having a transducer, such as a receiver or microphone. The present subject matter may be used in devices whether such devices are standard or custom fit and whether they provide an open or an occlusive design. It is understood that other hearing assistance devices not expressly stated herein may be used in conjunction with the present subject matter.

This application is intended to cover adaptations or variations of the present subject matter. It is to be understood that the above description is intended to be illustrative, and not restrictive. The scope of the present subject matter should be determined with reference to the appended claims, along with the full scope of legal equivalents to which such claims are entitled.

What is claimed is:

1. A hearing assistance device, comprising:
   a first housing configured to be worn above an ear of a wearer, the first housing including hearing assistance electronics;
   a second housing configured to be worn in the ear of the wearer, the second housing including a receiver configured to output signals processed by the hearing assistance electronics;
   a cable configured to connect to the first housing at a first end and to the second housing at a second end;
   one or more sensor modules at or near the second end of the cable, the one or more sensor modules configured to sense biometric signals from the wearer; and
   a sensor hub at or near the first end of the cable, the sensor hub including a processor configured to process data from the one or more sensor modules.

2. The device of claim 1, wherein the sensor hub is included in the cable.

3. The device of claim 1, wherein the sensor hub is included in a connect, plug at the first end of the cable.

4. The device of claim 1, wherein the sensor hub is configured to communicate with the one or more sensor modules using a serial interface over the cable.

5. The device of claim 1, wherein the sensor hub is configured to collate data from the one or more sensor modules and store the collated data in one or more logs.

6. The device of claim 5, wherein the one or more logs are configured for transmission to the hearing assistance electronics.

7. The device of claim 6, wherein the one or more logs are configured for continuous transmission to the hearing assistance electronics.

8. The device of claim 6, wherein the one or more logs are configured for on-demand transmission to the hearing assistance electronics.

9. The device of claim 1, wherein the device includes an inter-integrated circuit (I2C) bus connection from the hearing assistance electronics to the sensor hub.

10. The device of claim 1, wherein the device includes an inter-integrated circuit (I2C) bus connection from the sensor hub to the one or more sensor modules.

11. The device of claim 1, wherein the hearing assistance device is a receiver-in-the-canal (RIC) hearing aid.

12. A method, comprising:
sensing biometric signals from a wearer of a hearing assistance device using one or more sensor modules included in or on a receiver housing of the hearing assistance device, the receiver housing configured to connect to an end of a cable and configured to be placed in or near an ear canal of the wearer;
transmitting data indicative of the sensed biometric signals from the one or more sensor modules to a sensor hub in a connector of the cable; and
processing the data using the sensor hub.

13. The method of claim 12, wherein at least one of the one or more sensor modules includes a heart rate sensor.

14. The method of claim 12, wherein at least one of the one or more sensor modules includes a temperature sensor.

15. The method of claim 12, wherein at least one of the one or more sensor modules includes, an inertial measurement unit (IMU).

16. The method of claim 12, wherein at least one of the one or more sensor modules includes a blood pressure sensor.

17. The method of claim 12, wherein at least one of the one or more sensor modules includes a galvanic skin response (GSR) sensor.

18. The method of claim 12, wherein at least one of the one or more sensor modules includes a pulse transit time (PTT) sensor.

19. The method of claim 12, wherein at least one of the one or more sensor modules includes an oxygen (O2) sensor.

20. The method of claim 12, wherein at least one of the one or more sensor modules includes an electrocardiogram (ECG).

\* \* \* \* \*